Figure 1:
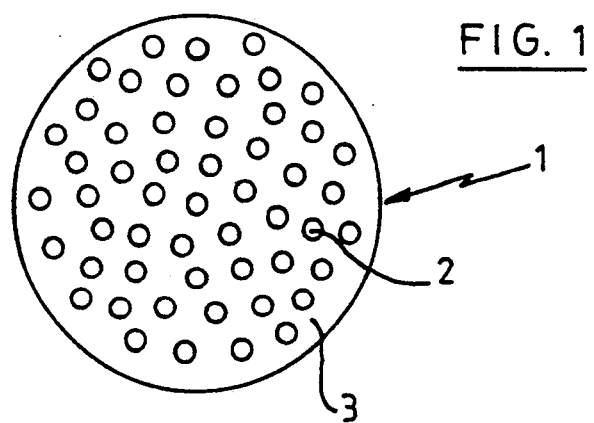

United States Patent [19]

Schacht et al.

[11] Patent Number: 5,407,682
[45] Date of Patent: Apr. 18, 1995

[54] PROCESS FOR THE PREPARATION OF AZO-AND /OR DISULFIDE POLYMER MATRIX DRUG DELIVERY SYSTEM FOR THE SITE SPECIFIC DELIVERY OF AN ACTIVE AGENT IN THE COLON

[75] Inventors: Etienne Schacht, Staden, Belgium; Ian Wilding, Bramcote, United Kingdom

[73] Assignee: Danbiosyst UK Ltd Aisha, United Kingdom

[21] Appl. No.: 915,689

[22] PCT Filed: Jan. 28, 1991

[86] PCT No.: PCT/BE91/00006
§ 371 Date: Sep. 9, 1992
§ 102(e) Date: Sep. 9, 1992

[87] PCT Pub. No.: WO91/11175
PCT Pub. Date: Aug. 8, 1991

[30] Foreign Application Priority Data

Jan. 29, 1990 [BE] Belgium .............................. 9000105

[51] Int. Cl.$^6$ ......................... A61K 9/22; A61K 47/34
[52] U.S. Cl. .................................. 424/436; 424/426; 424/468; 424/486; 424/482; 424/497

[58] Field of Search ................ 528/373; 424/426, 434, 424/427, 428, 78.08, 78.37, 486, 468, 482, 497

[56] References Cited

U.S. PATENT DOCUMENTS

| | | | |
|---|---|---|---|
| 3,909,497 | 9/1975 | Hendry et al. | 528/403 |
| 4,298,595 | 11/1981 | Parkinson et al. | 424/78.17 |
| 4,663,308 | 5/1987 | Saffran | 514/3 |
| 5,225,514 | 7/1993 | Kimura et al. | 528/85 |

Primary Examiner—Thurman K. Page
Assistant Examiner—Peter F. Kulkosky
Attorney, Agent, or Firm—Fitzpatrick, Cella, Harper & Scinto

[57] ABSTRACT

Azo-and/or disulfide-containing polymers for use as drug delivery systems having site-specific release of the drug in the colon are obtained by polycondensation or polyaddition of an azo- and/or polysulfide disulfide containing a, w-dihydroxy or diamino reagent with a suitable a, w-difunctional dicarboxylic acid; disocyanato-, disulfide comonomer. The resulting reduction sensitive polymers are linear macromolecules containing an azo and/or a disulfide bond in their polymer backbone.

12 Claims, 1 Drawing Sheet

PROCESS FOR THE PREPARATION OF AZO-AND /OR DISULFIDE POLYMER MATRIX DRUG DELIVERY SYSTEM FOR THE SITE SPECIFIC DELIVERY OF AN ACTIVE AGENT IN THE COLON

The present invention relates to a process for the preparation of azo- and/or disulfide- containing polymers to be used in the preparation of drug delivery systems providing a site specific delivery of the active agent in the colon.

The novel azo and disulfide containing polymers can be applied for preparing drug delivery systems that result in a site specific release of the drug in the lower part of the intestine.

It has been mentioned in the literature that the colon is a reductive medium and that enzymes are present which are able to cleave azo and disulfide bonds in organic molecules.

Peppercorn et al. published in Journal of Pharmacology and Experimental Therapy, 181, 555, 1972 that salicylazosulfapyridine (a drug applied for the therapeutic treatment of ulcerative colitis) (azuflidine, sulfasalazine) can be cleaved by microflora in the colon with release of 5-aminosalicylic acid.

U.S. Pat. Nos. 4,190,716 and 4,298,595 describe polymers having 5-aminosalicylic acid linked to a polymer backbone via an aromatic azo linkage which can be used for the site specific release of 5-aminosalicylic acid in the colon.

U.S. Pat. No. 4,663,308 describes the synthesis of a potentially crosslinked polymer obtained by radical copolymerization of vinyl monomers with an azo-containing comonomer which functions as a crosslinker during polymerization. A typical example of such an azo-containing crosslinker is 4,4'-divinylazobenzene. The resulting polymers were tested for the preparation of site selective drug delivery systems enabling the release of drug in the colon. Drug delivery systems can consist of systems coated by the azopolymer. The release of the enclosed drug is caused by enzymatic degradation of polymeric coating.

These systems have been proposed as a means to deliver drugs (e.g. peptides) via rectal and oral application to the colon.

Preliminary in vivo experiments with vasopressin containing dosage forms, coated with the azo-containing polymers, demonstrated the release of the peptide following oral administration of the novel dosage form. (Saffran, Journal of Pharmaceutical Sciences, 1988; Polymer Preprints, 1988; Science, 1986).

The azo-containing polymer systems described by Saffran all have in common their preparation via a copolymerization of vinyl-type monomers with substituted or nonsubstituted divinylazobenzene. This will ultimately lead to crosslinked polymers.

divinylazobenzene

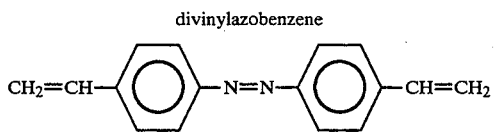

The disadvantage of this procedure is the possibility for crosslinkage of the polymer.

The polymers obtained after copolymerization of vinylmonomers with divinylazobenzene are to some extent crosslinked. Crosslinked polymers are insoluble and infusable. The reproducibility of preparing low degree crosslinked and still soluble polymers is anticipated to be very low.

The available literature learns that, not only azobonds but also disulfide bonds can be cleaved in the reductive medium that exists in the lower part of the G.I. tract, i.e. the colon.

The reductive potential in caecal contents has been reported in the literature, e.g. by H. Schroder and A. Johanssson (Xenobiotica, 3,4, 233–246, 1973). The potentials recorded ranged from $-100$ to $-400$ mV. This reductive medium is anticipated to be able to reduce disulfide bonds in organic compounds.

The disulfide bond in glutathione drug conjugates can be reduced in the colon and lead to liberation of the glutathion-linked thiol (G. L. Larsen, J. P. Larson, J. A. Gustarson, Fusobacterium necrophorum, Xenobiotica, 13, 689, 1983).

The objective of the presently described invention is the preparation of a series of azo- and disulfide-containing polymers which are susceptible to reductive cleavage in the gastro intestinal tract, i.e. in the colon, and which will be used for the preparation of colon specific drug delivery systems.

The method by which these reduction clearable polymers are prepared is the polycondensation or polyaddition of an $\alpha,\omega$-difunctional reagent with an appropriate $\alpha,\omega$-difunctional comonomer.

The reduction sensitive polymers are prepared according to the scheme shown below:

$$n\ Y\text{-}R_1\text{-}R\text{-}XX\text{-}R\text{-}R_2Y + n\ HX\text{-}R_3\text{-}XH \rightarrow Y\text{-}R_1\text{-}XX\text{-}R\text{-}R_2\text{-}[\text{-}Z\text{-}X\text{-}R_3\text{-}X\text{-}Z\text{-}R_1\text{-}R\text{-}XX\text{-}R\text{-}R_2\text{-}]_{n-1}\text{-}Z\text{-}X\text{-}R_3\text{-}XH$$

with
- $-XH = -NH_2$, $-OH$
- $-Y = -COOH$, CO-Hal, COOAlkyl, $-N=C=O$,

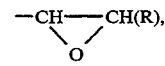

- $-SO_2Hal\text{-}XX\text{-}=\text{-}N=N\text{-}$, $-S\text{-}S\text{-}$ and
- $R = alkyl$,

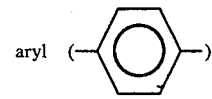

- $R_1$, $R_2$ = alkyl, aryl, alkylaryl groups all or not substituted
- $R_3$ = alkylidene, arylidene, alkylarylidene all or not substituted polyether, polyester
- hal = halogen radical, e.g. Cl, Br
- $Z = C=O$, $NH\text{-}C=O$, $CH_2\text{-}CH\text{-}OH$, $SO_2$ and whereby X and Y are interchangeable in the above formulas.

The functional groups in the above reaction equations are selected such that chemical reaction with formation of a covalent bond between the two reagents is feasible, e.g. ester formation, amid formation.

In the reaction with component $HX\text{-}R_3\text{-}XH$ the complementary reagent $Y\text{-}R_1\text{-}R\text{-}XX\text{-}R\text{-}R_2Y$ can be a diazo compound $(-XX\text{-}=\text{-}N=N\text{-})$ a disulfide compound $(-XX\text{-}=\text{-}S\text{-}S\text{-})$ or a mixture of both Composed such that the anticipated molarity of the complementary functional groups (Y-, resp. HX-) is respected.

The molecular weight of the polycondensation or polyaddition polymers generated through the above described reactions can be controlled by proper choice of the molarity of the complementary functional groups as commonly known in polymer synthesis.

The resulting reduction sensitive polymers are in principle linear, not crosslinked, macromolecules, containing an azo and/or a disulfide bond in their polymer backbone.

$$\sim\sim N=N\sim\sim N=N\sim\sim N=N\sim\sim N=N\sim\sim$$

or $$\sim\sim S-S\sim\sim S-S\sim\sim S-S\sim\sim S-S\sim\sim$$

or $$\sim\sim N=N\sim\sim S-S\sim\sim S-S\sim\sim N=N\sim\sim$$

This method allows the preparation of a series of azo and/or disulfide containing polymers through a variation in the $\alpha,\omega$-difunctional reagents. So the final physicochemical and physical properties (hydrophilicity, permeability, thermal properties, rheological properties) can be widely varied with the aim of using these polymers for preparing drug delivery systems. The latter can be matrix type systems or reservoir type systems. In the former case the azo and/or disulfide containing polymer is a major part of the drug containing compartment. In the latter part the azo and/or disulfide containing polymer is used to encapsulate a drug loaded core.

Provided these polymer are stable in the fluids of the mouth, the stomach and the upper intestine the herein described azo and/or disulfide- polymers can pass the mouth, stomach and upper intestine without being destructed. In the lower part of the G.I.-tract these reduction sensitive polymers can be cleaved and fragmented by the reductive medium, all or not enzym mediated. The enclosed active agent can be released at the site of degradation.

In a first approach to azo-containing polymers azobenzene-4,4'-dicarboxylic acid was used as one constructive part.

azobenzene-4,4'-dicarboxylic acid

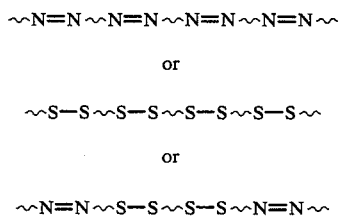

For condensation with the appropriate comonomers (HX-R$_3$-XH) the azobenzene-4,4'-dicarboxylic acid was transformed into a reactive derivative, such as a di-acidchloride, a di-paranitrophenolester, di-N-hydroxysuccinimid ester.

In one selected type of reaction an $\alpha,\omega$-difunctional azo reagent is reacted with an $\alpha,\omega$-dihydroxy or $\alpha,\omega$-diamino terminated comonomer, oligomer or polymer of the type of a polyether, polyester, polysiloxane, or vinylpolymer.

Disulfide containing polymers were prepared in a comparable manner as described above, by reacting 2,2'-dicarboxy diphenyldisulphide with an equimolar amount of an $\alpha,\beta$-dihydroxy or $\alpha\omega$-diamino terminated comonomer, oligomer or polymer of the type of a polyether, polyester, polysiloxane, or vinylpolymer.

2,2'-dicarboxy-diphenyldisulphide

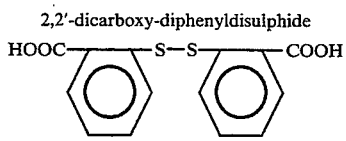

Reduction sensitive polymers containing azo and disulfide bonds were prepared by reacting a mixture of an azo containing diacid and a disulfide containing diacid with an equimolar amount of an $\alpha,\omega$-dihydroxy or $\alpha,\omega$-diamino terminated comonomer, oligomer or polymer of the type of a polyether, polyester, polysiloxane, or vinylpolymer.

Additional characteristics of the present invention will be illustrated in the hereunder described examples and figures.

These figures show:

FIG. 1.: A matrix device, e.g. a tablet, composed of a reductive azo and/or disulfide polymer FIG. 2.: A granule coated with a polymer film of the material described in this invention A first aspect of the present invention comprises the preparation of polymers containing in their backbone chain azo and/or disulfide groups. These are prepared by polycondensation or polyaddition of an $\alpha,\omega$-difunctional azo-containing and/or an $\alpha,\omega$-difunctional disulfide-containing reagent with an appropriate $\alpha,\omega$-comonomer.

The second aspect of the present invention comprises the use of the azo and/or disulfide containing polymers for the preparation of drug delivery systems.

The objective is to design dosage forms, retaining an active ingredient, which upon oral administration releases the active agent mainly during passage in the colon. This drug release is caused by degradation of the polymer, used to design the dosage form, in the reductive medium of the colon. The active agent being released in the colon can exert a local therapeutic action in the colon or being absorbed through the intestinal mucosa.

These dosage forms can be of different type:

a) dosage forms composed of a mixture of one or more active agents (drugs), an azo and/or disulfide containing polymer and possible additives b) dosage form composed of one or more drugs and one or more additives formulated in a practical form (tablet, granule, capsule). This dosage form is subsequently coated with a film of a reduction sensitive azo- and/or disulfide-containing polymer, all or not mixed with one or more additives. The reduction sensitive polymers are prepared according to the methods described in this invention.

I. DESCRIPTION OF THE STARTING MATERIALS

One example of an $\alpha,\omega$-difunctional azo compounds used to prepare the azo-containing polymers described in this invention is azo-benzene-4,4'-dicarboxylic and derivatives thereof:

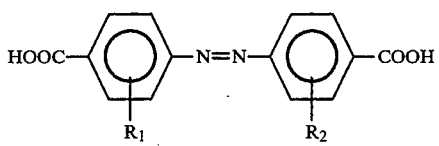

with $R_1$, $R_2$=alkyl, aryl, alkylaryl groups all or not substituted.

Examples of an α,ω-difunctional disulfide used to prepare the disulfide-containing polymers described in this invention are: 2,2'-dicarboxylic acid diphenyl disulfide, bis(2-carboxy ethyl) disulfide, bis(2-amino ethyl) disulfide and derivatives thereof:

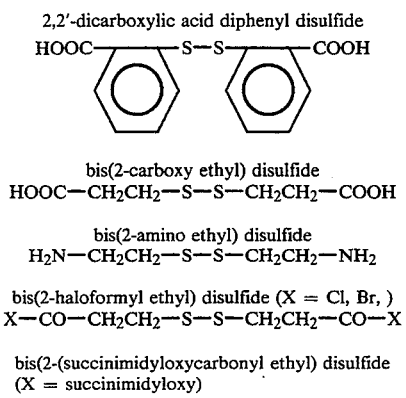

2,2'-dicarboxylic acid diphenyl disulfide bis(2-carboxy ethyl) disulfide
HOOC—CH$_2$CH$_2$—S—S—CH$_2$CH$_2$—COOH bis(2-amino ethyl) disulfide
H$_2$N—CH$_2$CH$_2$—S—S—CH$_2$CH$_2$—NH$_2$ bis(2-haloformyl ethyl) disulfide (X = Cl, Br, )
X—CO—CH$_2$CH$_2$—S—S—CH$_2$CH$_2$—CO—X bis(2-(succinimidyloxycarbonyl ethyl) disulfide
(X = succinimidyloxy)

First step
Preparation of azobenzene-4,4'-dicarboxylic acid.
Azobenzene-4,4'-dicarboxylic acid is prepared starting from 4-nitrobenzoic acid according to the method of Tomlinson (M. Tomlinson, Journal of Chemical society, 756 (1946)).

Example 1a
A mixture of 13 g 4-nitrobenzoic acid (0.078 mole) and 50 g NaOH (1.25 mole) in 225 ml of water is heated to 50° C. A solution of 100 g glucose (0.56 mole) in 150 ml water is added slowly over 15 minutes at 50° C. Then air is bubbled through the reaction mixture for a period of 48 h. The reaction medium is acidified with acetic acid to pH5. The carboxylic acid is removed by filtration, washed with aceton and ether and dried over phosphorous pentoxide.

Second step
Preparation of azobenzene-4,4'-diacid chloride
The azobenzene diacid can be subsequently converted into the diacidchloride, diacidbromide, or a di-reactive ester:

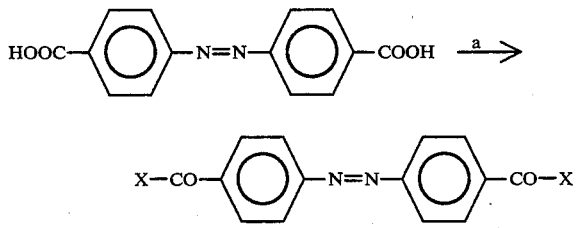

with a: a typical reagent well known from basic organic chemistry for this type of conversions.
a: SOX$_2$, SO$_2$X$_2$, POX$_3$, X-CO-CO-X and X=halogen radical, like Cl, Br.

Example 1b
To a solution of 10 g (0.074 mole) of azobenzene-4,4'-dicarboxylic acid and 5 ml of DMF in 50 ml toluene is added 45 ml (0.617 mole) SOCl$_2$. The reaction mixture is refluxed during 8 h. It is then filtered over a G-4 glass filter and allowed to cool-down to room temperature. The reaction product separates by crystallization. It is filtered off, recrystallized from isooctane and finally dried. The product is characterized by IR and NMR analysis: Typical IR adsorptions: -CO-Cl at 1770 cm$^{-1}$ aromatic C-H at 1580, 1540 cm$^{-1}$ Starting from the azobenzene dicarboxylic acid reactive esters such as 4-nitrophenyl esters, N-hydroxysuccinimide esters and alike can be prepared using conventional methods.

Third step
Preparation of bis(2-(succinimidyloxycarbonyl) ethyl) disulfide The bis-succinimidyl ester of the diacid disulfide can be prepared according to the method of Lomant and Fairbanks (A. J. Lomants, G. Fairbanks, J. Molecular Biology, 104,243, 1976).

Example 1c
6 g of bis(2-carboxy ethyl) disulfide is dissolved in 300 ml dry dioxane. To this is added 62 mmole N-hydroxysuccinimide and then 62,5 mmole N,N'-dicyclohexylcarbodiimide. The mixture is stirred for 24 h at room temperature with protection from moisture. The dicyclohexylurea is removed by filtration. The filtrate is then cooled and the dioxane removed by distillation under reduced pressure. The bis(2-succinimidyloxycarbonyl ethyl) disulfide is purified by repeated recrystallization from aceton/ether. The structure is confirmed by proton NMR.

Fourth step
As complementary α,ω-difunctional reagents to be used as comonomers with an α,ω-difunctional azocompound for the preparation of azo-containing polymers can be used:
a) for the reaction with an α,ω-dicarboxylic acid:
a α,ω-diamine or α,ω-diol of the type:

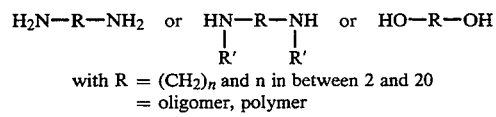

with R = (CH$_2$)$_n$ and n in between 2 and 20
= oligomer, polymer

As α,ω-hydroxy or amino terminated polymers or oligomers can be used polyethers, such as poly(ethylene oxide), poly(propylene oxide), copolymers of ethylene oxide and propyleneoxide (random or block copolymers), poly(tetramethylene oxide); polyesters such as polycaprolactone, poly(ethylene terephtalate), poly(butylene terephtalate); polydimethylsiloxane and vinyl polymers e.g. polybutadiene.

b) for the reaction with an α,ω-diamino azo compounds:
An α,ω-dicarboxylic acid of the type HOOC-R-COOH with R = (CH$_2$)$_n$ and n ranging between 2 and 20
= polymer or oligomer of the type polyether, polyester, polysiloxane or vinyl polymer as described under pt.a.

The α,ω-dihydroxy and α,ω-diamino reagents can be converted into the α,ω-diisocyanato derivatives by treatment with an appropriate quantity of a diisocyanate, e.g. hexamethylene diisocyanate, toluene diisocyanate, methylenediphenyl diisocyanate, etc.

A series of α,ω-dihydroxy and diamino terminated polymers are commercially available. In addition α,ω-dihydroxy terminated polymers and oligomers can be transformed into the α,ω-diamino terminated polymers by methods well known in organic chemistry.

II. EXAMPLES FOR METHODS TO PREPARE AZO- AND/OR DISULFIDE CONTAINING POLYMERS

For the preparation of the azo-containing polymer the α,ω-difunctional azo-containing reagent can be replaced partially by another α,ω-difunctional reagent which contains no azo bonds whereby the functional groups are of the same nature as those in the azo-containing reagent. The latter type of α,ω-difunctional reagent may be one containing a disulfide bond.

In an analogous way for the preparation of the disulfide-containing polymer the α,ω-difunctional disulfide-containing reagent can be replaced partially by another α,ω-difunctional reagent which contains no disulfide bonds whereby the functional groups are of the same nature as those in the disulfide-containing reagent. The latter type of α,ω-difunctional reagent may be one containing an azo bond.

As an example in the preparation of an azo-containing polymer starting from azobenzene-4,4'-dicarboxylic acid part of the azodiacid can be replaced by dicarboxylic acids like oxalic acid, succinic acid, terephtalic acid, bis(2-carboxy ethyl) disulfide, etc.

In the synthesis of these polymers the molecular weight can be controlled by adjusting the molar ratios of the functional groups reacting with one another.

For the preparation of high molecular weight polymers equivalent amounts of the functional groups that react with one another must be used.

The polycondensation or polyaddition reaction can be carried out in solution or in a two phaze system.

As an example azo-containing polymer can be prepared by reacting azobenzene-4,4'-diacidchloride with α,ω-diamino poly(tetramethylene oxide) in solution (e.g. in chloroform) and in presence of an acid acceptor like triethylamine.

A number of α,ω-diamino terminated polymers or oligomers are commercially available. They also can be prepared by chemical modification of their α,ω-dihydroxy terminated analogues.

Example 2

Preparation of α,ω-amino terminated poly(ethylene oxide) starting from dihydroxy terminated polymer 45 g poly(ethylene oxide) is dissolved in 400 ml dry benzene. While stirring under an inert atmosphere 8 g butyl lithium is added. Then 35 g tosylchloride dissolved in 100 ml of dry benzene is added and the solution is stirred for 12 h at room temperature. The lithium chloride formed during reaction is removed by filtration and the filtrate is concentrated by evaporation. The residue is redissolved in dry ethanol and cooled at −20° C. The ditosylate precipitates and can be isolated by filtration and dried.

5 g ditosylate ester of poly(ethylene oxide) is dissolved in 250 ml concentrated ammonia and placed in an autoclave at 120°. The solution is then allowed to cool to room temperature and is concentrated. The residue is dissolved in 20 ml 1N sodium carbonate and extracted with toluene. The organic layer is concentrated by evaporation. The residue is dried over phosphorous pentoxide.

In a similar manner other α,ω-dihydroxy terminated polymers like poly(tetramethylene oxide), can be converted into the α,ω-diamino terminated derivatives.

Other examples use carboxy-terminated polymers which either are commercially available or can be prepared starting from the α,ω-dihydroxy or diamino terminated polymers using techniques described in the literature.

Example 3a

Preparation of an azo-containing polymer by reaction of azobenzene-4,4'-dicarbonylchloride with α,ω-diamino terminated poly(tetramethylene oxide).

Reaction sheme

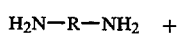

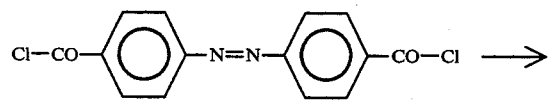

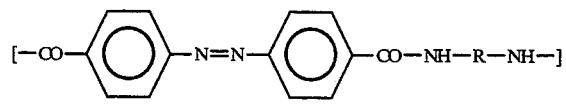

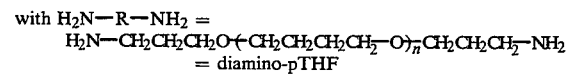

Experimental part

The polyamide is prepared by a solution polycondensation. To a solution of 10 g (5 meq) diamino-pTHF (MW 750) dissolved in 100 ml chloroform is added 7 ml of triethylamine (50 meq). The mixture is stirred for 15 min. at −10° C. Then 3.85 g (25 meq) azobenzene-4,4'-diacidchloride, dissolved in 75 ml chloroform, is added. The mixture is stirred for 24 h at room temperature, extracted with 0.1N HCl, subsequently 0.1N NaOH. The chloroform layer is dried over magnesium sulfate. The solvent is then stripped off. The reaction product is characterized via IR and NMR analysis.

IR-adsorptions: -CO-NH-: 1640, 1540 cm$^{-1}$; aromatic C-H: 1600 cm$^{-1}$. The molecular weight of the polymer as determined by gel permeation chromatography is 26,300.

In a similar manner azopolymers can be prepared by polycondensation of azobenzene-4,4'-dicarbonyl chloride and an α,ω-diamino-terminated poly(ethylene oxide -co- propylene oxide).

The polycondensation can be carried out in solution or in a two phaze system (interfacial polymerization).

The resulting polymers are essentially linear non-crosslinked macromolecules.

Example 3b

Preparation of an azo-polymer by reaction of azobenzene 4,4'diacid chloride and α,ω-diamino poly(ethyleneoxide-copropyleneoxide).

Reaction sheme

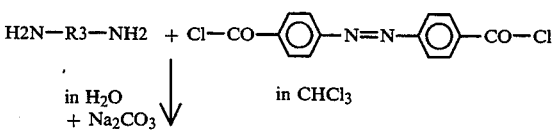

-continued

Reaction sheme

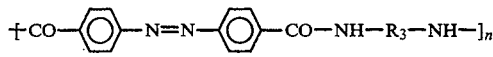

with H2N—R3—NH2
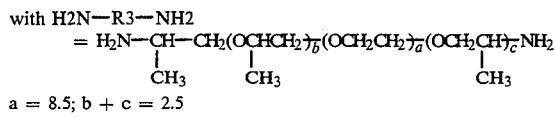

a = 8.5; b + c = 2.5

In this example the polyamide is prepared by an interfacial polycondensation.

Experimental 2 g (65.15 meq) Jeffamine ED-600 and 1.38 g (30 meq) Na2CO3 are added to a stirred 250 ml mixture of chloroform/water (1:2, v:v). log (65.15 meq) azobenzene-4,4'-diacidchloride dissolved in 125 ml dry chloroform is added. Then the mixture is stirred at room temperature for 6 h. The organic layer is isolated, washed with HCl and NaOH, dried and evaporated. The resulting reaction product is characterized by IR and NMR.

IR absorptions: -CO-NH- 1650, 1535 cm$^{-1}$ aromatic: 1600 cm$^{-1}$

Molecular weight (GPC): 16,400

Example 4

Preparation of a disulfide-containing polymer by reaction of bis(2-(succinimidyloxycarbonyl)ethyl) disulfide with an diamino poly(tetramethylene oxide) (amino-pTHF).

H2N—R—NH2 +

X—CO—CH2CH2—S—S—CH2CH2—CO—X ⟶

[—CO—CH2CH2—S—S—CH2CH2—CO—NH—R—NH—]

with H2N—R—NH2 =
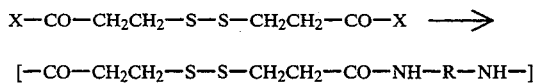
= diamino-pTHF and

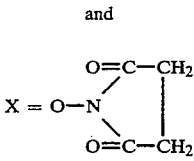

Experimental

To a solution of 4.7 g (11.95 meq) diamino-pTHF (MW: 750) in 40 ml dry chloroform is added 3.3 ml triethylamine (23.7 meq), and 2.41 g (11.95 meq) bis(2-succinimidyloxycarbonyl ethyl) disulfide. The reaction mixture is stirred for 24 h at room temperature. The chloroform layer is then extracted with O.1N HCl and phosphate buffer pH7, resp. the organic layer is dried over MgSO4 and concentrated under reduced pressure. The structure of the polymer is confirmed by IR and NMR.

In a similar experiment as described in the examples 3b and 4 polymers containing azo and disulfide groups have been prepared by condensing a mixture of an $\alpha,\omega$-difunctional azo-containing reagent and an $\alpha,\omega$-difunctional disulfide containing reagent with an appropriate complementary $\alpha,\omega$-difunctional reagent.

III. APPLICATIONS OF AZO- AND/OR DISULFIDE- CONTAINING POLYMERS IN DRUG DELIVERY

1. Matrix systems

Polymers of the type as described in the present invention can be used as matrix component (indicated in FIG. 1 by the number 1) in the preparation of drug delivery systems. In such dosage forms the active agent is dissolved or dispersed in a matrix partially or completely composed of an azo- and/or disulfide containing polymer.

Dosage forms of this type can be obtained by impregnation of a preformed matrix with a solution of one or more active agents.

Example 5

10 g azo-containing polymer obtained by reaction of azobenzene-4,4'-dicarbonylchloride and an $\alpha,\omega$-diamino terminated poly(tetramethylene oxide) is mixed with 1 g salicylazosulfapyridine. 0.5 g of the powdered mixture is placed in a matrix with an internal diameter of 1 cm. Using a heated press, the mixture is compressed for 2 min at 100° C. and at 100 kN. After removal from the matrix a homogeneous tablet is obtained.

Alternatively the dosage forms can be prepared by compressing a mixture composed of azo- and/or disulfide-containing polymer, One or more drugs, one or more additives in the form of a tablet or pill, or by extrusion of the mixture.

Examples of acceptable additives are vegatable or animal oils and fats, anorganic or organic polymers, e.g. poly(ethylene oxide), poly(vinylpyrrolidone), microcrystalline cellulose, starch, hydroxypropyl methylcellulose, magnesium stearate, talc, lactose, silica and other additives.

2. Polymer coated systems

Figure 2:
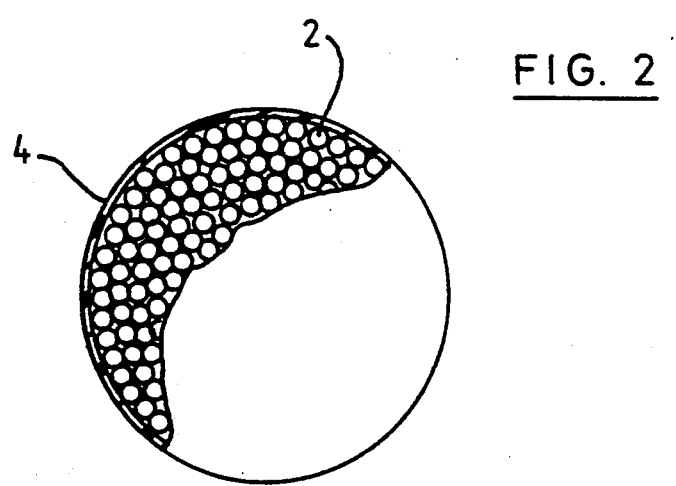

The above azo- and/or disulfide containing polymers (4 in FIG. 2) described in this invention can be used for the coating of existing dosage forms (2 in FIG. 2). This coating can occur by applying a solution or a suspension of the azo- or disulfide polymers. Coating can be performed using well known standard techniques (e.g. spraying, dip coating).

The coating film (4) is selected such that after oral administration of the dosage form the polymer film is degraded selectively in the color, whereby the drug is being released.

Example 6

Preparation of hydrogel spheres, loaded with oxprenolol, and coated with an azo-containing polymer.

5 g of hydrogel beads (polyHEMA, crosslinked with 0.5% glycol dimethacrylate, average diameter 500 μm) are suspended in 50 ml of a 20% (wt) solution of oxprenolol in methylene chloride. After 24 h the beads are removed by filtration, washed with one portion of 20 ml chloroform and dried in a rotary evaporator. Extraction experiments and HPLC analysis indicated the drug content being 11%. These drug loaded beads are placed in a miniaturized fluidized bed coater and sprayed with a 10% solution of the azo-containing polymer (example 3) in chloroform. Azo-polymer coated beads are obtained. The average coating thickness can be varied, one example: thickness=50 μm.

We claim

1. A process for the preparation of a drug delivery system for the site specific delivery of an active agent in the colon comprising the steps of: (a) preparing a colon specific reduction sensitive polymer selected from the group consisting of (i) azo-containing polymers, (ii) disulfide-containing polymers and (iii) azo- and disulfide-containing polymers, by copolymerizing an azo- and/or disulfide-containing $\alpha,\omega$-difunctional reagent by polycondensation or polyaddition with a suitable $\alpha,\omega$-difunctional comonomer according to the general reaction sheme illustrated below:

n Y-R$_1$-R-XX-R-R$_2$Y + n HX-R$_3$-XH→Y-R$_1$-R-XX-R-R$_2$-[-Z-X-R$_3$-X-Z-R$_1$-R-XX-R-R$_2$-]$_{n-1}$-Z-X-R$_3$-XH with
-XH = -NH$_2$, -OH
-Y = -COOH, CO-Hal, COOAlkyl, -N=C=O,

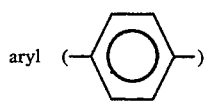

-SO$_2$Hal, -COOSuccinimide
-XX- = -N=N-, -S-S-
and
R = alkyl, aryl (—⟨O⟩—)

R$_1$, R$_2$ = alkyl, aryl, alkylaryl groups all or not substituted
R$_3$ = alkylidene, arylidene, alkylarylidene all or not substituted polyether, polyester
hal = halogen radical, e.g. Cl, Br
with: -Y + H-X→-Z-X
and Z = C=O, NH-C=O, CH$_2$-CH-OH, SO$_2$
and whereby X and Y are interchangeable in the above formulas; and (b) compounding or coating said active agent with said polymer to form said drug delivery system capable of providing a site specific delivery of said active agent in the colon.

2. The process according to claim 1, wherein said azo-containing $\alpha,\omega$-difunctional reagent is azobenzene-4,4'-dicarboxylic acid.

3. The process according to claim 1, wherein said azo-containing $\alpha,\omega$-difunctional reagent dis azobenzene-4,4'-diacidchloride.

4. The process according to claim 1, wherein said disulfide-containing $\alpha,\omega$-difunctional reagent is bis(2-(succinimidyloxycarbonyl)ethyl) disulfide.

5. The process according to claim 1, wherein said disulfide-containing $\alpha,\omega$-difunctional reagent is bis(2-carboxyethyl) disulfide.

6. The process according to claim 1, wherein said disulfide-containing $\alpha,\omega$-difunctional reagent is bis(2-(chloroformyl)ethyl) disulfide.

7. The process according to claim 1, wherein said $\alpha,\omega$-difunctional comonomer is an $\alpha,\omega$-dihydroxy- or $\alpha,\omega$-diamino-terminated monomer, oligomer or polymer selected from the group consisting of ethers, polyethers, esters, polyesters, siloxane, polysiloxane, alkene, arylene, alkyarylene and a vinyl polymer.

8. The process according to claim 1, wherein said step of compounding comprises formulating said active agent in a matrix containing the colon specific reduction sensitive polymer.

9. The process according to claim 1, wherein said step of coating comprises coating a dosage unit containing said active agent with the colon specific reduction sensitive polymer.

10. The process according to claim 1, wherein said azo-containing polymer is formed by the process comprising the step of mixing (i) said $\alpha,\omega$-difunctional comonomer dissolved in chloroform and triethylamine with (ii) azobenzene-4-4'-diacid-chloride dissolved in chloroform for a time and at a temperature sufficient to form said azo-containing polymer.

11. The process according to claim 4, wherein bis(2-(succinimidyloxycarbonyl)ethyl) disulfide is prepared by the process comprising the step of adding N-hydroxysuccinimide and N, N'-dicyclohexylcarbodiimide to a solution of bis(2-carboxy-ethyl) disulfide dissolved in dioxane for a time and at temperature sufficient to form bis (2-(succinimidyloxycarbonyl) ethyl) disulfide.

12. A colon specific drug delivery system prepared according to the process of claim 1.

* * * * *

UNITED STATES PATENT AND TRADEMARK OFFICE
CERTIFICATE OF CORRECTION

PATENT NO. : 5,407,682

DATED : April 18, 1995

INVENTOR(S) : ETIENNE SCHACHT, ET AL.

It is certified that error appears in the above-indentified patent and that said Letters Patent is hereby corrected as shown below:

ON THE TITLE PAGE:
[54] Title

"AZO-AND" should read --AZO- AND--.

[57] Abstract

Line 1, "Azo-and/or" should read --Azo- and/or--;

Line 4, "polysulfide" should be deleted;

Line 5, "a, ω-dihydroxy" should read --α,ω-dihydroxy--; and

Line 6, "a, ω-disfunctional" should read --α,ω-disfunctional--; and "acid; disocyana-" should read --acid, diisocyana- --.

COLUMN 1

Line 1, "AZO-AND" should read --AZO- AND--.

COLUMN 2

Line 33, "Y-$R_1$-XX-R-$R_2$-" should read --Y-$R_1$-R-XX-R-$R_2$- --; and

Line 68, "Composed" should read --composed--.

UNITED STATES PATENT AND TRADEMARK OFFICE
CERTIFICATE OF CORRECTION

PATENT NO. : 5,407,682

DATED : April 18, 1995

INVENTOR(S) : ETIENNE SCHACHT, ET AL.

It is certified that error appears in the above-indentified patent and that said Letters Patent is hereby corrected as shown below:

COLUMN 3

Line 36, "polymer" should read --polymers--;

Line 38, "disulfide-" should read --disulfide--; and

Line 68, "αω-diamino" should read --α,ω-diamino--.

COLUMN 4

Line 24, "polymer" should read --polymer,--;

Line 27, "invention" should read --invention.--; and

Line 51, "additives" should read --additives.--.

COLUMN 6

Line 18, "disulfide The" should read --disulfide. ¶ The--;

Line 54, "terephtalate," should read --terephthalate,--; and

Line 55, "terephtalate);" should read --terephthalate);--.

COLUMN 7

Line 30, "terephtalic" should read --terephthalic--; and

Line 37, "react-with" should read --react with--.

UNITED STATES PATENT AND TRADEMARK OFFICE
CERTIFICATE OF CORRECTION

PATENT NO. : 5,407,682
DATED : April 18, 1995
INVENTOR(S) : ETIENNE SCHACHT, ET AL.

It is certified that error appears in the above-indentified patent and that said Letters Patent is hereby corrected as shown below:

COLUMN 8

Line 54, "phaze" should read --phase--.

COLUMN 9

Line 17, "log" should read --10g--;

Line 30, "an diamino" should read --an α,ω-diamino--; and

Line 57, "O.1N HCl" should read --0.1N H Cl--.

COLUMN 10

Line 2, "DISULFIDE -CONTAINING" should read --DISULFIDE-CONTAINING--;

Line 30, "vegatable" should read --vegetable--;

Line 31, "anorganic" should read --inorganic--;

Line 46, "color," should read --colon,--; and

Line 64, "claim" should read --claim:--.

Signed and Sealed this

Second Day of January, 1996

Attest:

BRUCE LEHMAN

Attesting Officer        Commissioner of Patents and Trademarks